United States Patent
Blumenfeld et al.

(10) Patent No.: US 10,729,751 B2
(45) Date of Patent: *Aug. 4, 2020

(54) INJECTION PARADIGM FOR ADMINISTRATION OF BOTULINUM TOXINS

(71) Applicant: Allergan, Inc., Irvine, CA (US)

(72) Inventors: Andrew M. Blumenfeld, Del Mar, CA (US); Mitchell F. Brin, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/173,664

(22) Filed: Oct. 29, 2018

(65) Prior Publication Data
US 2019/0060423 A1 Feb. 28, 2019

Related U.S. Application Data

(63) Continuation of application No. 15/067,515, filed on Mar. 11, 2016, now Pat. No. 10,111,938.

(60) Provisional application No. 62/132,689, filed on Mar. 13, 2015.

(51) Int. Cl.
*A61K 38/48* (2006.01)
*A61K 9/00* (2006.01)

(52) U.S. Cl.
CPC ........ *A61K 38/4893* (2013.01); *A61K 9/0019* (2013.01); *C12Y 304/24069* (2013.01)

(58) Field of Classification Search
None
See application file for complete search history.

(56) References Cited

U.S. PATENT DOCUMENTS

| | | |
|---|---|---|
| 5,714,468 A | 2/1998 | Binder |
| 6,306,423 B1 | 10/2001 | Donovan |
| 6,312,708 B1 | 11/2001 | Donovan |
| 6,585,993 B2 | 7/2003 | Donovan |
| 7,704,511 B2 | 4/2010 | Turkel |
| 7,811,587 B2 | 10/2010 | Donovan |
| 2005/0191320 A1 | 9/2005 | Turkel |
| 2005/0191321 A1 | 9/2005 | Turkel et al. |
| 2010/0266638 A1 | 10/2010 | Turkel |
| 2013/0224180 A1 | 8/2013 | Turkel ............... A61K 38/4893 424/94.67 |

FOREIGN PATENT DOCUMENTS

WO 2011-123456 10/2011

OTHER PUBLICATIONS

Johnson, Eric, Clostridial Toxins as Therapeutic Agents: Benefits of Nature's Most Toxic Proteins, Annu Reb Microbiol, 1999, 551-575, 53.
Emer et al., "Injectable neurotoxins and fillers: There is no free lunch", Clinics in Dermatology 2011, vol. 29, pp. 678-690.

*Primary Examiner* — Michelle F. Paguio Frising
(74) *Attorney, Agent, or Firm* — Brigitte C. Phan

(57) ABSTRACT

Disorders such as headaches can be treated by administration of a botulinum toxin to a patient suffering therefrom, such as a migraine headache. A combined a fixed site/fixed dose and an optional follow the pain variable dosage and injection site paradigm is disclosed for optimizing clinical effectiveness of botulinum toxin administration for patients suffering headache, particularly chronic migraine.

29 Claims, 15 Drawing Sheets

FOREHEAD ANATOMY

CORRUGATORS

The procerus produces transverse lines over the bridge of the nose

PROCERUS

PROCERUS

FRONTALIS

Frontalis muscles are elevator muscles, meaning they pull the brow upward.

Frontalis muscles are involved in drawing the scalp forward, creating transverse lines on the forehead

FRONTALIS

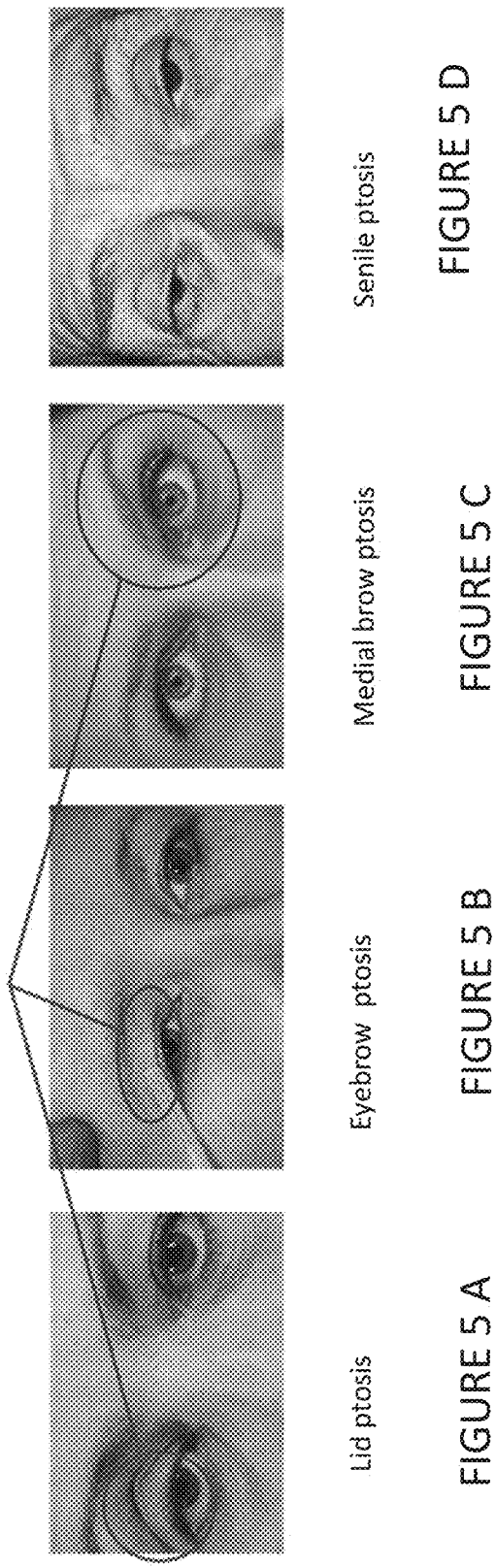
FIGURE 5 A  Lid ptosis
FIGURE 5 B  Eyebrow ptosis
FIGURE 5 C  Medial brow ptosis
FIGURE 5 D  Senile ptosis

TEMPORALIS

BACK-OF-HEAD AND NECK ANATOMY

OCCIPITALIS

CERVICAL PARASPINAL MUSCLES

INJECTION PARADIGM FOR ADMINISTRATION OF BOTULINUM TOXINS

CROSS REFERENCE TO RELATED APPLICATIONS

This application is a Continuation of U.S. application Ser. No. 15/067,515, filed Mar. 11, 2016, now U.S. Pat. No. 10,111,938, which claims the benefit of U.S. Provisional patent application No. 62/132,689 filed Mar. 13, 2015 and may be related to U.S. patent application Ser. No. 13/075,485 filed Mar. 30, 2011, now U.S. Pat. No. 8,501,195, incorporated entirely by reference.

FIELD

Embodiments of the present invention relate to the treatment of various disorders, specifically to injection administration protocols utilizing botulinum neurotoxins. In particular, the present disclosure is directed to methods for improving administration protocols for treatment of chronic migraine.

BACKGROUND

It is known that botulinum toxins can be utilized to treat a variety of disorders. Examples include U.S. Pat. No. 5,714,468 (migraine) issued Feb. 3, 1998; Published U.S. Patent Application No. 2005019132 (headache), Ser. No. 11/039,506, filed Jan. 18, 2005; Published U.S. Patent Application No. 20050191320 (medication overuse headache), Ser. No. 10/789,180, filed Feb. 26, 2004; and U.S. Pat. No. 7,811,587 (neuropsychiatric disorders), issued Oct. 12, 2010; all incorporated entirely by reference.

An example of a disorder treatable with botulinum toxins is chronic migraine (CM), a disabling headache disorder, affecting 1.3% to 2.4% of the general population and considered the most common type of primary chronic daily headache in the United States. CM is linked with suffering, disability, and medication overuse, and only one third of CM patients use headache prophylactic medication. Few headache preventive treatments have been investigated for patients with CM. Thus there remains a need for optimized and targeted methodologies to treat this malady in particular, specific and useful injection and dosage paradigms for utilizing botulinum toxins to treating CM.

SUMMARY

In one embodiment, the present invention teaches a method for prophylactically treating a headache in a patient suffering from chronic migraine headaches, the method comprises of local administration of a clostridial neurotoxin, such as a botulinum neurotoxin, to the frontalis, corrugator, procerus, occipitalis, temporalis, trapezius and cervical paraspinal muscles of the patient that suffers from the migraine headache, where the botulinum neurotoxin is administered, to the frontalis at about twenty units divided among four sites of injection, to the corrugator at about ten units divided among two sites of injection; to the procerus at about five units to one site of injection; to the occipitalis at about thirty units divided among six sites of injection to about forty units divided among eight sites of injection; to the temporalis at about forty units divided among eight sites of injection up to fifty units divided among ten sites of injection; to the trapezius at about thirty units divided among six sites of injection up to about fifty units divided among ten sites of injection and to the cervical paraspinal muscles at about twenty units divided among four sites of injection, and where the botulinum neurotoxin is injected at 31 to 39 injection sites.

In some aspects, the present disclosure is directed to a method for reducing the occurrence or alleviating a headache in a patient suffering from chronic migraine headaches in a patient with chronic migraine headaches, the method comprises: localizing one or more administration target; isolating the one or more administration target; administering a therapeutically effective amount of a clostridial toxin to the isolated one or more administration target; wherein the one or more administration target comprises the frontalis, corrugator, procerus, occipitalis, temporalis, trapezius and cervical paraspinal muscles; wherein the administrating step is by injection and wherein the administering step comprises limiting the injection to a defined tissue depth and injection angle.

In some aspects, the present disclosure is directed to a method for improving efficacy of headache treatment by a clostridial toxin, such as a botulinum toxin, in a patient in need thereof by minimizing adverse effects associated with clostridial toxin administration, comprising localizing one or more administration target, isolating the one or more administration target, administering a therapeutically effective amount of the clostridial toxin to the isolated one or more administration target, wherein the administrating step is by injection and wherein the administering step comprises limiting the injection to a defined tissue depth and injection angle. In some embodiments, the adverse effects include ptosis, neck pain/weakness, headache, or combinations thereof. In some embodiments, the method further comprises evaluating the patient for manifestations of adverse effects prior to the locating, isolating and administrating steps. In some embodiments, the method further comprises informing the patient of the manifestation of adverse effects.

In some aspects, the present disclosure provides a method for minimizing adverse effects associated with the administration of a clostridial toxin, such as a botulinum toxin, for treating or alleviating a headache in a patient with chronic migraine, the method comprises locating one or more administration target, isolating the one or more administration target, administering a therapeutically effective amount of a clostridial toxin to the isolated one or more administration target; wherein the administrating step is by injection and wherein the administering step comprises limiting the injection to a defined tissue depth and injection angle. In some embodiments, the adverse effects comprise ptosis, neck pain and/or weakness, headache, or combinations thereof. In some embodiments, the present method further increases patient compliance in timely getting re-treatment.

The present method also comprises assessing a patient for pre-existing conditions prior to clostridial toxin treatment for expectation management, selecting a suitable injection protocol to minimize aggravating the pre-existing conditions or delaying the clostridial toxin administration until the pre-existing conditions improve. In some embodiments, the pre-existing conditions include ptosis, neck pain or weakness, headache, or combinations thereof.

The present method further comprises identifying a patient who may be prone to having clostridial toxin administration associated adverse effects, informing the patient of the risk of adverse effects and selecting a suitable injection protocol to prevent or minimize the risk of adverse effects. In some embodiments, the adverse effects include ptosis, neck pain or weakness, headache, or combinations thereof.

BRIEF DESCRIPTION OF THE DRAWING FIGURES

The following drawings are presented to illustrate aspects and features of embodiments of the present invention.

FIGS. 1A and 1B show the forehead anatomy, identifying one or more administration target sites thereof in accordance with one embodiment of the present injection paradigm;

FIGS. 2A-2D detail the anatomy, the administration sites, and injection technique for administrating a botulinum toxin into the corrugator muscle in accordance with aspects of the present method;

FIGS. 3A-3D detail the anatomy, the administration site, and injection technique for administrating a botulinum toxin into the procerus muscle in accordance with aspects of the present method;

FIGS. 4A-4D detail the anatomy, the administration sites, and injection technique for administrating a botulinum toxin into the frontalis muscle in accordance with aspects of the present method;

FIGS. 5 A-5D show some examples of ptosis;

FIGS. 6A-6D detail the anatomy, the administration sites, and injection technique for administrating a botulinum toxin into the temporalis muscle in accordance with aspects of the present method;

DESCRIPTION

Figure 1B:
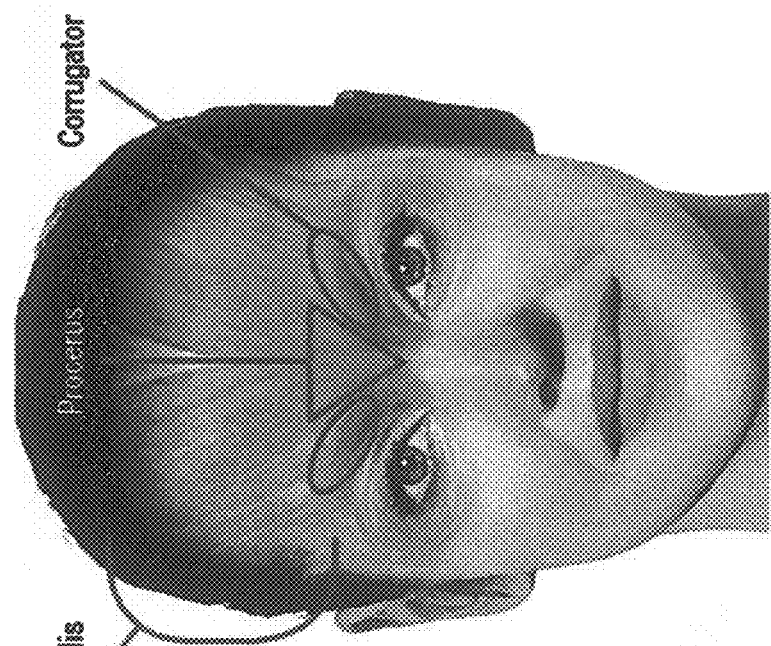

In certain embodiments, the dose of a botulinum toxin used according to embodiments of the present invention is less than the amount of botulinum toxin that would be used to paralyze a muscle, because an intent of a method according to embodiments of the present invention is not to paralyze a muscle but to reduce a pain sensory output from sensory neurons located in or on a muscle, or in or under the skin.

The following definitions apply herein:

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Administration", or "to administer" means the step of giving (i.e. administering) a botulinum toxin to a subject, or alternatively a subject receiving a pharmaceutical composition. The present method can be performed via administration routes including intramuscular, non-intramuscular, intra-articular, extra-articular, peri-articular, intradermal, subcutaneous administration, topical administration (using liquid, cream, gel or tablet formulation), intrathecal administration, intraperitoneal administration, intravenous infusion, implantation (for example, of a slow-release device such as polymeric implant or miniosmotic pump), or combinations thereof.

"Alleviating" means a reduction of an undesirable condition or its symptoms, for example headache intensity or headache-associated symptoms. Thus, alleviating includes some reduction, significant reduction, near total reduction, and total reduction. An alleviating effect may not appear clinically for between 1 to 7 days after administration of a clostridial derivative to a patient or sometime thereafter.

"Botulinum toxin" means a neurotoxin produced by *Clostridium botulinum*, as well as a botulinum toxin (or the light chain or the heavy chain thereof) made recombinantly by a non-Clostridial species. The term "botulinum toxin", as used herein, encompasses the botulinum toxin serotypes A, B, $C_1$, D, E, F and G, and their subtypes and any other types of subtypes thereof, or any re-engineered proteins, analogs, derivatives, homologs, parts, sub-parts, variants, or versions, in each case, of any of the foregoing. "Botulinum toxin", as used herein, also encompasses a "modified botulinum toxin". Further "botulinum toxin" as used herein also encompasses a botulinum toxin complex, (for example, the 300, 600 and 900 kDa complexes), as well as the neurotoxic component of the botulinum toxin (150 kDa) that is unassociated with the complex proteins.

"Clostridial derivative" refers to a molecule which contains any part of a clostridial toxin. As used herein, the term "clostridial derivative" encompasses native or recombinant neurotoxins, recombinant modified toxins, fragments thereof, a Targeted vesicular Exocytosis Modulator (TEM), or combinations thereof.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate.

"Effective amount" as applied to the biologically active ingredient means that amount of the ingredient which is generally sufficient to induce a desired change in the subject.

"Implant" means a controlled release (e.g., pulsatile or continuous) composition or drug delivery system. The implant can be, for example, injected, inserted or implanted into a human body.

"Local administration" means administration of a clostridial derivative to or to the vicinity of a symptomatic site in a patient by a non-systemic route. Thus, local administration excludes systemic routes of administration, such as intravenous or oral administration.

"Peripheral administration" means administration to a location away from a symptomatic location, as opposed to a local administration.

"TEMs", abbreviated for Targeted Exocytosis Modulators are retargeted endopeptidases that direct the catalytic activity of the light chain to specific types of neuronal cells or to target cells that were not affected by botulinum toxins expanding the beneficial clinical effect of inhibition of exocytosis in several human diseases.

"Treating" or "treatment" means to prevent, reduce the occurrence, alleviate, or to eliminate an undesirable condition, for example headache, either temporarily or permanently.

"Therapeutically effective amount" refers to an amount sufficient to achieve a desired therapeutic effect. The therapeutically effective amount usually refers to the amount administered per injection site per patient treatment session, unless indicated otherwise.

Disclosed herein are embodiments of an administration paradigm for botulinum neurotoxins. In some embodiments, the method can include specific administration locations and dosage amounts of a botulinum toxin to treat various disorders, including, for example, chronic migraine (CM), Medication overuse (MOU), neuropsychiatric (ND) disorders, and the like. In certain embodiments of the invention, the disorder can be treated by intramuscular administration of the toxin in specific amounts or ranges of amounts to specific sites within the upper torso of the patient. In certain embodiments, such sites can include, for example, the head, the neck, one or both shoulders, in both the anterior or posterior positions.

In some embodiments, the clostridial derivative of the present method includes a native, recombinant clostridial toxin, recombinant modified toxin, fragments thereof, targeted exocytosis modulators (TEMs), or combinations thereof. In some embodiments, the clostridial derivative is a botulinum toxin. In alternative embodiments, the clostridial derivative is a TEM.

In some embodiments, the botulinum neurotoxin can be a modified neurotoxin, that is a botulinum neurotoxin which has at least one of its amino acids deleted, modified or replaced, as compared to a native toxin, or the modified botulinum neurotoxin can be a recombinant produced botulinum neurotoxin or a derivative or fragment thereof. In certain embodiments, the modified toxin has an altered cell targeting capability for a neuronal or non-neuronal cell of interest. This altered capability is achieved by replacing the naturally-occurring targeting domain of a botulinum toxin with a targeting domain showing a selective binding activity for a non-botulinum toxin receptor present in a non-botulinum toxin target cell. Such modifications to a targeting domain result in a modified toxin that is able to selectively bind to a non-botulinum toxin receptor (target receptor) present on a non-botulinum toxin target cell (re-targeted). A modified botulinum toxin with a targeting activity for a non-botulinum toxin target cell can bind to a receptor present on the non-botulinum toxin target cell, translocate into the cytoplasm, and exert its proteolytic effect on the SNARE complex of the target cell. In essence, a botulinum toxin light chain comprising an enzymatic domain is intracellularly delivered to any desired cell by selecting the appropriate targeting domain.

In some embodiments, the clostridial derivative is a botulinum toxin, which is selected from the group consisting of botulinum toxin types A, B, $C_1$, D, E, F and G. In one embodiment, the clostridial derivative of the present method is a botulinum toxin type A. The botulinum toxin can be a recombinant botulinum neurotoxin, such as botulinum toxins produced by *E. coli*.

The clostridial derivative, such as a botulinum toxin, for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as, for example, albumin, or the like. Acceptable excipients or stabilizers include protein excipients, such as albumin or gelatin, or the like, or non-protein excipients, including poloxamers, saccharides, polyethylene glycol, or the like. In embodiments containing albumin, the albumin can be, for example, human serum albumin or recombinant human albumin, or the like. The lyophilized material can be reconstituted with a suitable liquid such as, for example, saline, water, or the like to create a solution or composition containing the botulinum toxin to be administered to the patient.

In some embodiments, to increase the resident time of the clostridial derivative in the joint, the clostridial derivative is provided in a controlled release system comprising a polymeric matrix encapsulating the clostridial derivative, wherein fractional amount of the clostridial derivative is released from the polymeric matrix over a prolonged period of time in a controlled manner. Controlled release neurotoxin systems have been disclosed for example in U.S. Pat. Nos. 6,585,993; 6,585,993; 6,306,423 and 6,312,708, each of which is hereby incorporated by reference in its entirety.

The therapeutically effective amount of the clostridial derivative, for example a botulinum toxin, administered according to the present method can vary according to the potency of the toxin and particular characteristics of the condition being treated, including its severity and other various patient variables including size, weight, age, and responsiveness to therapy. The potency of the toxin is expressed as a multiple of the $LD_{50}$ value for the mouse, one unit (U) of toxin being defined as being the equivalent amount of toxin that kills 50% of a group of 18 to 20 female Swiss-Webster mice, weighing about 20 grams each.

The therapeutically effective amount of the botulinum toxin according to the present method can vary according to the potency of a particular botulinum toxin, as commercially available Botulinum toxin formulations do not have equivalent potency units. For example, one unit of BOTOX® (onabotulinumtoxinA), a botulinum toxin type A available from Allergan, Inc., has a potency unit that is approximately equal to 3 to 5 units of DYSPORT® (abobotulinumtoxinA), also a botulinum toxin type A available from Ipsen Pharmaceuticals. In some embodiments, the amount of abobotulinumtoxinA, (such as DYSPORT®), administered in the present method is about three to four times the amount of onabotulinumtoxinA (such as BOTOX®) administered, as comparative studies have suggested that one unit of onabotulinumtoxinA has a potency that is approximately equal to three to four units of abobotulinumtoxinA. MYOBLOC®, a botulinum toxin type B available from Elan, has a much lower potency unit relative to BOTOX®. In some embodiments, the botulinum neurotoxin can be a pure toxin, devoid of complexing proteins, such as XEOMIN® (incobotulinumtoxinA). One unit of incobotulinumtoxinA has potency approximately equivalent to one unit of onabotulinumtoxinA. The quantity of toxin administered, and the frequency of its administration will be at the discretion of the physician responsible for the treatment and will be commensurate with questions of safety and the effects produced by a particular toxin formulation.

The amount of the botulinum toxin administered according to a method within the scope of embodiments of the invention can vary according to the particular characteristics of the pain being treated, including its severity and other various patient variables including size, weight, age, and responsiveness to therapy.

To guide the practitioner, typically, no less than about 1 unit and no more than about 25 units of a botulinum toxin type A (such as BOTOX®) is administered per injection site per patient treatment session. For a botulinum toxin type A such as DYSPORT®, no less than about 2 units and no more than about 25 units of the botulinum toxin type A are administered per injection site, per patient treatment session. For a botulinum toxin type A such as DYSPORT®, no less than about 2 units and no more than about 125 units of the botulinum toxin type A are administered per injection site, per patient treatment session. For a botulinum toxin type B such as MYOBLOC®, no less than about 40 units and no more than about 1500 units of the botulinum toxin type B are administered per injection site, per patient treatment session.

Preferably, for BOTOX® no less than about 2 units and no more about 20 units of a botulinum toxin type A are administered per injection site per patient treatment session; for DYSPORT® no less than about 4 units and no more than about 100 units are administered per injection site per patient treatment session; and; for MYOBLOC®, no less than about 80 units and no more than about 1000 units are administered per injection site, per patient treatment session.

More preferably, for BOTOX® no less than about 5 units and no more about 15 units of a botulinum toxin type A; for DYSPORT® no less than about 20 units and no more than about 75 units, and; for MYOBLOC®, no less than about 200 units and no more than about 750 units are, respectively, administered per injection site, per patient treatment session.

Generally, the total amount of BOTOX®, DYSPORT® or MYOBLOC®, suitable for administration to a patient according to the methods of the invention disclosed herein should not exceed about 300 units, about 1,500 units or about 15,000 units respectively, per treatment session.

The treatment effects of the botulinum toxin can persist for between about 1 month and about 5 years.

Embodiments of the present disclosure provide a targeted, fixed injection paradigm directed to a specific set of muscles with a specific minimum number and volume of injections, and further provides for the additional/optional administration of additional botulinum toxin to specific site of selected muscles. In one embodiment, the fixed dosage (that is, a minimum dosage amount in accordance with the fixed amounts and locations specified in a package insert or prescribing information) of botulinum toxin is administered to the frontalis, corrugator, procerus, occipitalis, temporalis, trapezius and cervical paraspinal muscles of a patient, and further a variable amount of additional botulinum toxin can be added to four or less of the seven head/neck areas such that the total amount of botulinum toxin administered does not exceed a maximum total dosage as indicated in the package insert or prescribing information accompanying a botulinum toxin-containing medicament.

The botulinum toxin can be selected from the group consisting of botulinum toxin types A, B, C, D, E, F and G. Botulinum toxin type A is a preferred botulinum toxin. The botulinum toxin can be administered in an amount of between about 1 unit and about 3,000 units, or between about 2 units and about 2000 units, or between about 5 units and about 1000 units, or between about 10 units and about 500 units, or between about 15 units and about 250 units, or between about 20 units and about 150 units, or between 25 units and about 100 units, or between about 30 units and about 75 units, or between about 35 units and about 50 units, or the like, and the alleviation of the symptoms can persist for between about 1 month and about 5 years.

In one embodiment, a method is disclosed that utilizes a dose and injection paradigm of 155 units of BOTOX® (typically provided as 100 Units of *Clostridium botulinum* type A neurotoxin complex, with 0.5 mg of human serum albumin, and 0.9 mg of sodium chloride in a sterile, vacuum-dried state for reconstitution), administered as 31 fixed-site, fixed-dose (5 units) injections, and an optional 40 units in up to 8 additional injection sites using a follow-the-pain regimen per treatment cycle (for up to 39 injection sites and up to 195 units total). The total dose is divided across 7 head/neck muscles and is repeated every 12 weeks.

In an embodiment, a method for treating a migraine such as, for example, CM, can encompass administration of a botulinum toxin to 31 fixed injection sites across seven head/neck muscles. Optionally, up to 8 additional injection sites into three specific muscles, where these three muscles are subset of the above seven head/neck muscles, are administered utilizing a follow-the pain regimen to provide flexibility in the dose/muscle for the three muscles, to address individual patient needs. In particular embodiments, a minimum of 155 units of a botulinum toxin type A up to about 195 units of a botulinum toxin type A, are administered in accordance with a particular injection paradigm herein disclosed.

In a specific embodiment, a method for treating CM comprises the step of local administration of a botulinum neurotoxin to the frontalis, corrugator, procerus, occipitalis, temporalis, trapezius and cervical paraspinal muscles of the CM patient such that the botulinum neurotoxin is administered to the frontalis at about twenty units divided among four sites of injection, to the corrugator at about ten units divided among two sites of injection, to the procerus at about five units to one site of injection, to the occipitalis at about thirty units divided among six sites of injection to about forty units divided among eight sites of injection; to the temporalis at about forty units divided among eight sites of injection up to fifty units divided among ten sites of injection, to the trapezius at about thirty units divided among six sites of injection up to about fifty units divided among ten sites of injection and to the cervical paraspinal muscles at about twenty units divided among four sites of injection, such that the total amount of botulinum neurotoxin administered is from about 155 units to about 195 units injected at from 31 to 39 injection sites, respectively.

Embodiments of the invention can also be used as part of a detoxification protocol whereby a patient who is being weaned off acute pain medications is facilitated in this goal by concurrent administration of a botulinum toxin. Additional embodiments of the invention can be used to treat other chronic pain conditions, including, for example, back pain, neuropathic pain, allodynia, fibromyalgia, and the like.

In an embodiment, a method for treating an MOU patient can encompass administration of a botulinum toxin to 31 fixed injection sites across seven head/neck muscles. Optionally, up to 8 additional injection sites into three specific muscles, where these three muscles are subset of the above seven head/neck muscles, are administered utilizing a follow-the pain regimen to provide flexibility in the dose/muscle for the three muscles, to address individual patient needs. In particular embodiments, a minimum of 155 units of a botulinum toxin type A up to about 195 units of a botulinum toxin type A, are administered in accordance with a particular injection paradigm herein disclosed.

In a specific embodiment, a method for treating MOU comprises the step of local administration of a botulinum neurotoxin to the frontalis, corrugator, procerus, occipitalis, temporalis, trapezius and cervical paraspinal muscles of the MOU patient such that the botulinum neurotoxin is administered to the frontalis at about twenty units divided among four sites of injection, to the corrugator at about ten units divided among two sites of injection, to the procerus at about five units to one site of injection, to the occipitalis at about thirty units divided among six sites of injection to about forty units divided among eight sites of injection; to the temporalis at about forty units divided among eight sites of injection up to fifty units divided among ten sites of injection, to the trapezius at about thirty units divided among six sites of injection up to about fifty units divided among ten sites of injection and to the cervical paraspinal muscles at about twenty units divided among four sites of injection, such that the total amount of botulinum neurotoxin administered is from about 155 units to about 195 units injected at from 31 to 39 injection sites, respectively.

In an embodiment, a method for treating depression can encompass administration of a botulinum toxin to 31 fixed injection sites across seven head/neck muscles. Optionally, up to 8 additional injection sites into three specific muscles, where these three muscles are subset of the above seven head/neck muscles, are administered utilizing a follow-the-pain regimen to provide flexibility in the dose/muscle for the three muscles, to address individual patient needs. In particular embodiments, a minimum of 155 units of a botulinum toxin type A up to about 195 units of a botulinum toxin type A, are administered in accordance with a particular injection paradigm herein disclosed.

In a specific embodiment, a method for treating neuropsychiatric disorders (ND) such as, for example, depression, in a patient in need thereof comprises the step of local administration of a botulinum neurotoxin to the frontalis, corrugator, procerus, occipitalis, temporalis, trapezius and cervical paraspinal muscles of the patient such that the botulinum neurotoxin is administered to the frontalis at about twenty units divided among four sites of injection, to the corrugator at about ten units divided among two sites of injection, to the procerus at about five units to one site of injection, to the occipitalis at about thirty units divided among six sites of injection to about forty units divided among eight sites of injection; to the temporalis at about forty units divided among eight sites of injection up to fifty units divided among ten sites of injection, to the trapezius at about thirty units divided among six sites of injection up to about fifty units divided among ten sites of injection and to the cervical paraspinal muscles at about twenty units divided among four sites of injection, such that the total amount of botulinum neurotoxin administered is from about 155 units to about 195 units injected at from 31 to 39 injection sites, respectively.

A method for treating or reducing the occurrence of a headache in a patient with chronic migraine has been disclosed in U.S. Pat. No. 8,501,195 to Turkel (hereinafter "the '195 patent" or "the Turkel patent").

The '195 patent teaches a method for treating a headache in a patient suffering from chronic migraine headaches, the method essentially consisting of local administration of a botulinum neurotoxin to the frontalis, corrugator, procerus, occipitalis, temporalis, trapezius and cervical paraspinal muscles of the patient that suffers from the migraine headache, where the botulinum neurotoxin is administered, to the frontalis at about twenty units divided among four sites of injection, to the corrugator at about ten units divided among two sites of injection; to the procerus at about five units to one site of injection; to the occipitalis at about thirty units divided among six sites of injection to about forty units divided among eight sites of injection; to the temporalis at about forty units divided among eight sites of injection up to fifty units divided among ten sites of injection; to the trapezius at about thirty units divided among six sites of injection up to about fifty units divided among ten sites of injection and to the cervical paraspinal muscles at about twenty units divided among four sites of injection, and where the botulinum neurotoxin is injected at 31 to 39 injection sites.

The treatment taught by the '195 patent (hereinafter "the '195 treatment" or "the Turkel treatment") has been practiced by health care practitioners with high efficacy to treat or reduce the occurrence of a headache in a patient with chronic migraine. In one embodiment, the '195 patent teaches a method for treating chronic migraine that utilizes a dose and injection paradigm of 155 units of onabotulinumtoxinA, administered as 31 fixed-site, fixed-dose (5 units per) injections, and an optional 40 units in up to 8 additional injection sites using a follow-the-pain regimen per treatment cycle (for up to 39 injection sites and up to 195 units total). The total dose is divided across 7 head/neck muscles and is repeated every 12 weeks.

The inventors of the present disclosure have discovered that compliance to the treatment protocol of "a minimum dose of 155 units divided across 7 head/neck muscles and repeated every 12 weeks" is not optimally consistent due to adverse effects which will be described herein. These adverse effects are attributable to improper, imprecise or inaccurate implementation of the '195 protocol, which results in inadvertent and undesirable administration of the botulinum toxin into an area adjacent to an administration target site and/or too deep injections into sensitive structures. Because of these adverse effects, selected administration targets of the '195 treatment method may be intentionally left out (such as for example some forehead and neck muscles), which reduces the efficacy of the treatment method. These adverse effects may also discourage patients from timely seeking re-treatments. This delay further reduces the efficacy of the headache treatment.

In some aspects, the present disclosure provides a method for minimizing adverse effects associated with the administration of a botulinum toxin for treating or alleviating a headache in a patient with chronic migraine. In some embodiments, the adverse effects comprise ptosis, neck pain and/or weakness, headache, or combinations thereof. By minimizing the adverse effects associated with administration of a botulinum toxin for treating or alleviating a headache, the present method enhances efficacy of the treatment and increases patient compliance in timely getting re-treatment, which further increases efficacy treatment.

The present method also comprises assessing a patient for pre-existing conditions prior to botulinum toxin treatment for expectation management, selecting a suitable injection protocol to minimize aggravating the pre-existing conditions or delaying the botulinum toxin administration until the pre-existing conditions improve. The pre-existing conditions include ptosis, neck pain or weakness, headache, or combinations thereof.

The present method further comprises identifying a patient who may be prone to having botulinum toxin administration associated adverse effects, including ptosis, neck pain or weakness, headache, or combination thereof, informing the patient of the risk of adverse effects, selecting a suitable injection protocol to prevent or minimize the risk of adverse effects, or delay the botulinum toxin until the risk of adverse effects is reduced.

To increase efficacy of botulinum toxin treatment for headache/migraine and/or to minimize or eliminate the above-identified adverse effects, the present method comprises locating the administration target, isolating the administration target so that the botulinum toxin is administered only to the isolated target area without inadvertently impacting an adjacent area; controlling the injection depth, and angling the needle as to aim away from sensitive structures. In some embodiments, the administration target includes the 7 head/neck muscles taught by the '195 patent.

Figure 1A:
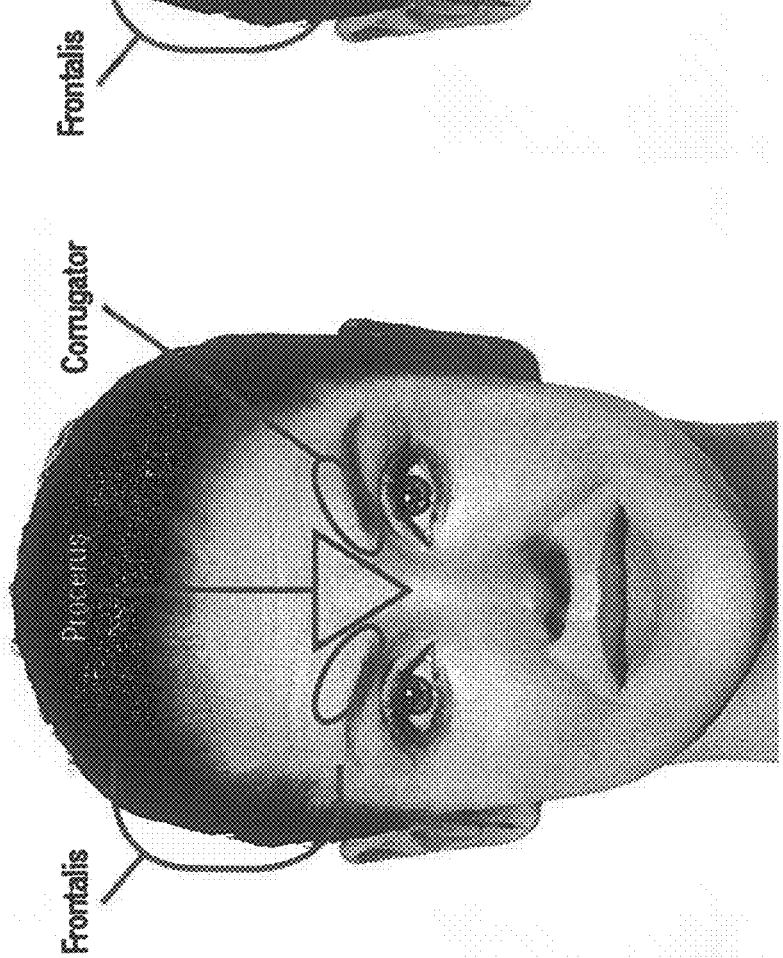

FIGS. 1A and 1B show the forehead anatomy, identifying the location of exemplary administration target sites, including the corrugator, procerus and frontalis muscles.

Figure 2B:
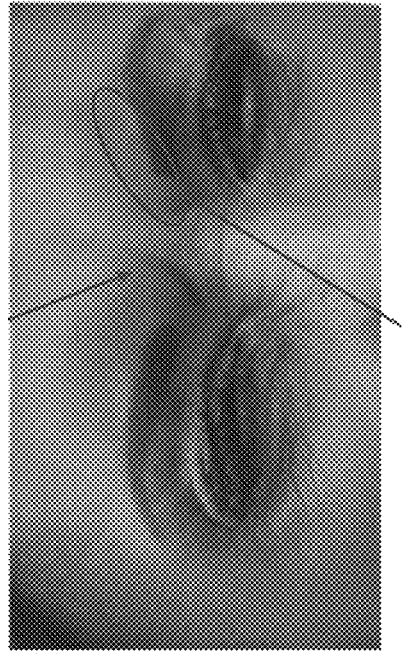
Figure 2A:
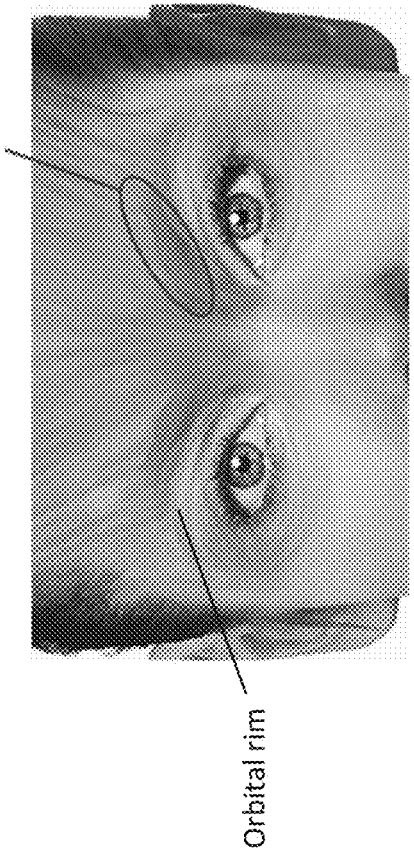
Figure 2D:
Figure 2C:
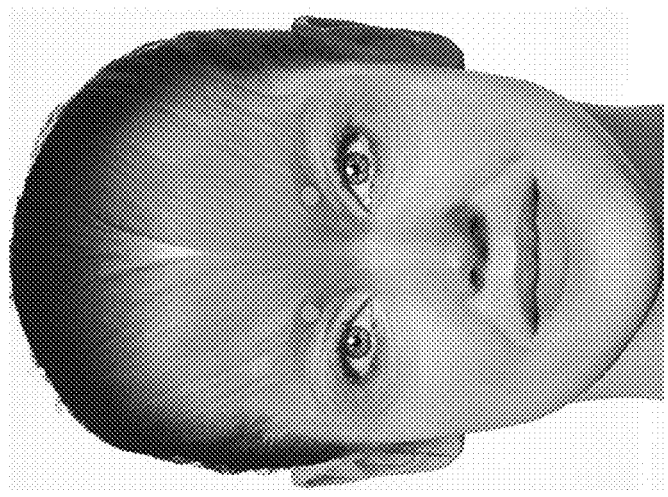

Corrugator:

In one exemplary embodiment, as shown schematically in FIG. 2C, the present method comprises local administration of a botulinum neurotoxin to the corrugator at about ten units divided among two sites of injection. As shown in FIG. 2A, the corrugator muscle is located about 1.5 cm or ~1 fingerbreadth above the medial inferior edge of the orbital rim, a bony landmark which can be used to localize the corrugator. This distance may vary depending on individual anatomy. Thus, administrating of the botulinum neurotoxin based solely on the approximated distance of 1.5 cm or fingerbreadth approach may lead to inadvertent penetration of the frontalis muscle, which can result in brow ptosis. Furthermore, pointing the needle upward at a 45 degree angle laterally may also result in inadvertent penetration of the frontalis. Corrugators are thin muscles, thus injecting too deep can hit the periosteum and may trigger a headache/migraine.

To minimize or prevent unwarranted side effects, in some embodiments, the present method comprises locating the corrugator, isolating the corrugator to eliminate or minimize inadvertent injection to the frontalis and administering a botulinum toxin to the corrugators. As shown in FIG. 2A, the corrugator muscle is located about 1.5 cm or ~1 fingerbreadth above the medial inferior edge of the orbital rim, a bony landmark which can be used to localize the corrugator. In some embodiments, the locating step comprises localizing the orbital rim and the corrugator muscle situated in the proximity thereof. The corrugators produce vertical lines on the portion of the skin below the head between the brows, as seen in FIG. 2B. In some embodiments, the isolating step comprises providing patient instructions to furrow her/his brow, which activates the corrugator and causing medial and inferior movement of the brow (FIG. 2B). In some embodiments, the isolating step further comprises palpating and pinching the corrugator muscle, holding them between the thumb and index finger, as shown in FIG. 2D. The corrugators are brow depressors, meaning they pull the brow down. They attach to the nasal frontal bone medially and the skin of the eye brow laterally. To further minimize or eliminate brow ptosis, in some embodiments, the administering step comprises targeting the belly of the corrugators (FIG. 2B). In some embodiments, the administrating step comprises injecting at a 90° angle into the belly of the corrugator muscles, as shown in FIGS. 2B and 2D. In some embodiments, the administering step further comprises controlling the penetration depth of the needle such that it remains above the periosteum.

In some embodiments, the present disclosure discloses a method for minimizing or eliminating adverse effects associated with botulinum toxin administration for treatment of headache, the method comprises locating the corrugator muscle, isolating the corrugator muscle, administrating a botulinum neurotoxin to the corrugator muscle at about ten units divided among two sites of injection, wherein the locating step comprises localizing the orbital rim and the corrugator muscle in the proximity thereof, the isolating step comprises providing a patient instructions to furrow her/his brow, palpating and pinching the corrugator muscle, holding them between the thumb and index finger; and wherein the administrating step comprises superficially injecting at a 90° degree angle into the corrugator muscle. In some embodiments, superficially injecting comprises controlling the penetration depth of the needle such that it remains above the periosteum.

Figure 3B:
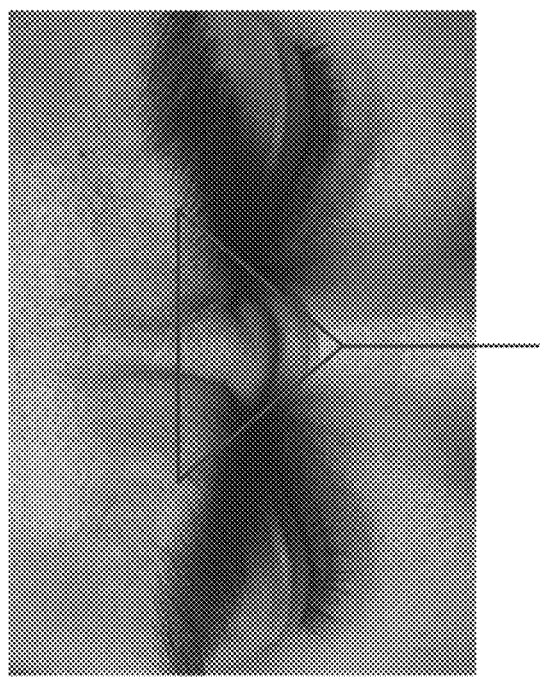
Figure 3A:
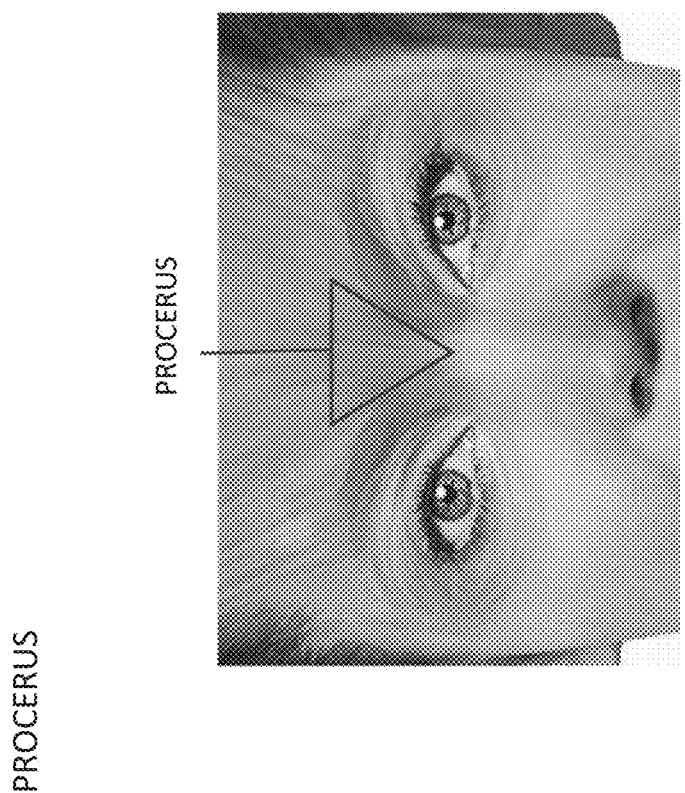
Figure 3D:
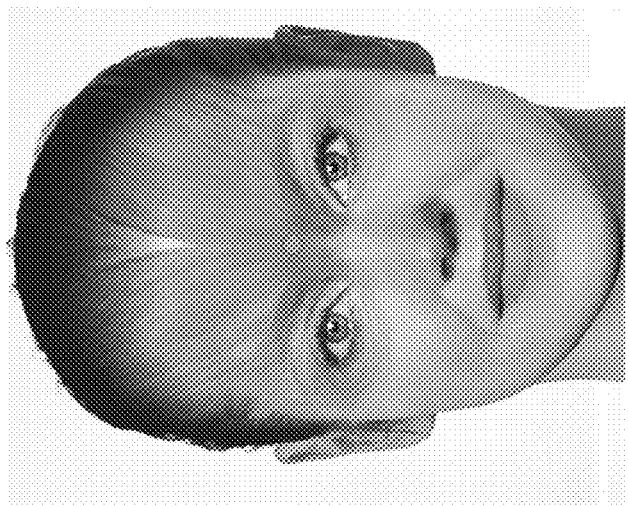
Figure 3C:

Procerus:

In one exemplary embodiment, as shown schematically in FIG. 3C, the present method further comprises local administration of a botulinum neurotoxin to the procerus at about five units. As shown in FIG. 3A, the procerus muscle is between the brows, and not in the forehead. Relatively, the base of the procerus is located approximately midway between the two corrugators injections (FIGS. 3C and 2C). This distance may vary depending on individual anatomy. Thus, administrating of the botulinum neurotoxin based solely on the approximated distance approach may lead to inadvertent penetration of the frontalis muscle, which can result in medial brow depression. Injecting too high in the brow area in the lower frontalis can also lead to brow ptosis. The procerus muscle is thin, thus injecting too deep can hit the periosteum and may trigger a headache/migraine.

To minimize or prevent unwarranted side effects, in some embodiments, the present method comprises locating the procerus, isolating the procerus to eliminate or minimize inadvertent injection to the frontalis and administering a botulinum toxin to the procerus. In some embodiments, the locating step comprises localizing the administration sites for the corrugators as set forth above and finding the base of the procerus located midway between the two corrugator injections. As shown in FIG. 3B, the procerus draws down the medial angle of the eyebrow and produces transverse lines over the bridge of the nose. In some embodiments, the isolating step comprises providing a patient instructions to furrow her/his brow, and using the resulting vertical and horizontal lines as orientation lines (FIG. 3B). In some embodiments, the administering step comprises targeting the belly of the procerus muscle, which may be visible between the corrugator lines (FIG. 3D). In some embodiments, the administrating step comprises injecting superficially at a 90° angle into the procerus, as shown in FIG. 3D. In some embodiments, the administering step further comprises controlling the penetration depth of the needle such that it remains above the periosteum.

Figure 4A:
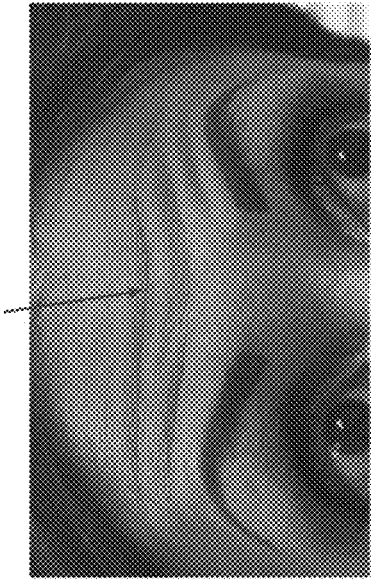
Figure 4B:
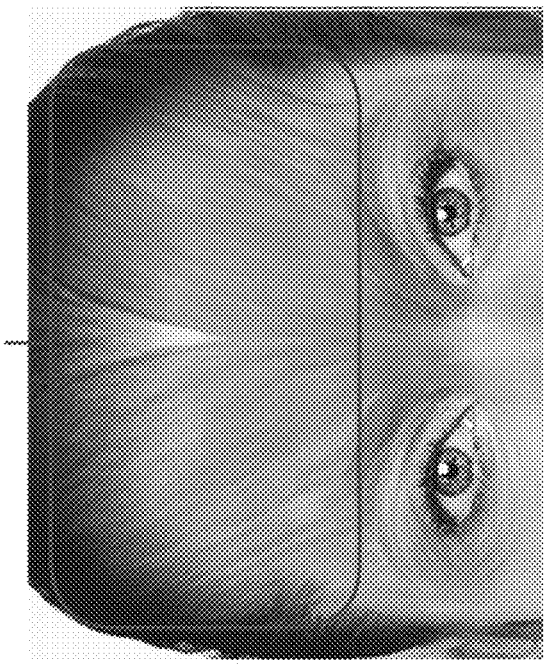
Figure 4C:

Frontalis:

In some embodiments, as shown schematically in FIG. 4C, the present method further comprises local administration of a botulinum neurotoxin to the frontalis at about twenty units divided among four sites of injection. In some prior art protocol, to localize the medial frontalis muscle for administration of botulinum toxin, a line is drawn from the medial edge of the supraorbital rim and the muscle areas for injections are approximated about 1.5 cm (~1 fingerbreadth) above the corrugator injection site. The lateral frontalis muscle is localized as the area parallel and about 1.5 cm (~1 fingerbreadth) lateral to the medial injection area, which is approximately in line with the midpupillary line or the lateral limbic line. All foreheads are different shapes and sizes. Thus, administrating of the botulinum neurotoxin based solely on the approximated distance or fingerbreadth approach may lead to low injections, which can cause medial brow weakness and lateral brow elevation. Furthermore, the frontalis muscles are elevator muscles, meaning that they pull the brow upward. Unduly, inadvertently or improperly weakening these muscles may cause or exacerbate brow ptosis. The frontalis muscles are thin, thus injecting too deep can hit the periosteum and may trigger a headache/migraine.

Figure 4D:
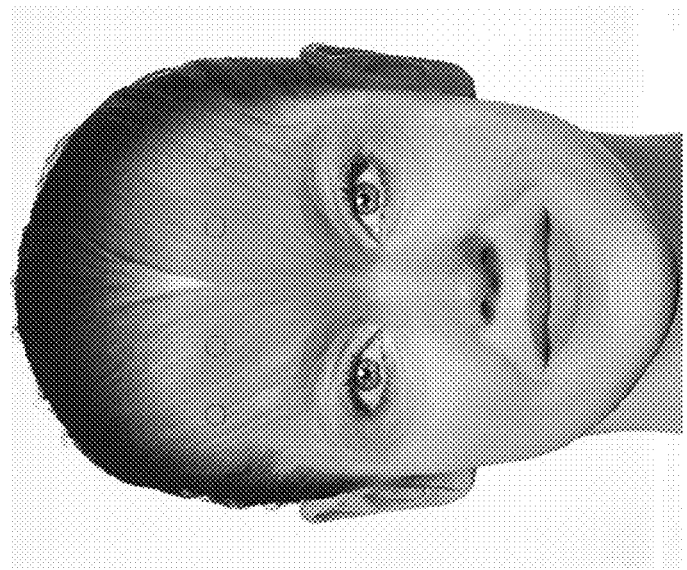

To minimize or prevent unwarranted side effects, including brow weakness, brow elevation, brow ptosis, in some embodiments, the present method comprises locating the frontalis muscle, isolating administration target area within the frontalis and administering a botulinum toxin to the frontalis. In some embodiments, the locating step comprises defining the medial and lateral area for neurotoxin administration. In some embodiments, defining the medial muscle area comprises drawing a line up from the medial edge of the supraorbital rim and the administration target areas are about 1.5 cm above the corrugator administration site. In some embodiments, the lateral muscle area for neurotoxin administration is parallel and about 1.5 cm lateral to the medial administration site. In some embodiments, the frontalis administration sites are in line with the midpupillary line or the lateral limbic line. As set forth above, this approach alone may lead to low injections. The frontalis muscles are involved in drawing the scalp forward, creating transverse lines on the forehead as well as in raising eyebrow and skin over the root of the nose, as shown in FIG. 4B. In some embodiments, the isolating step comprises providing patient instructions to raising her/his eyebrows and skin over the root of the nose, such as creating an expression of surprise (FIG. 4B). In some embodiments, the isolating step comprises identifying the upper third of the forehead (FIG. 4D). In some embodiments, the administrating step comprises angling the needle superiorly at a 45° angle into the frontalis muscle, as shown in FIG. 4D. As the needle is angled at 45°, the medication delivery site may be different from the administration site. In some embodiments, the administration step comprises injecting superficially by controlling the penetration depth of the needle such that it remains above the periosteum. In some embodiments, a local and topical anesthetic is administered before administration of the neurotoxin to minimize discomfort.

In some embodiments, the present method further comprises assessing a patient's forehead for signs or symptoms of ptosis prior to botulinum toxin administration botulinum toxin, informing the patient of the existence of ptosis, and administrating a botulinum toxin to the administration targets, including the corrugators, procerus, frontalis muscles, or combinations thereof, as disclosed herein.

FIGS. 5A-5D show pictures of various manifestations of ptosis. Manifestations of ptosis comprise a drooping eyelid as shown in FIG. 5A, excessive skin under the brow as shown in FIG. 5B, medial brow depression and/or lateral brow elevation as shown in FIG. 5C. The lid ptosis (FIG. 5A), eyebrow ptosis (FIG. 5b) and medial brow ptosis (FIG. 5C) can result from prior botulinum toxin administrations. Senile ptosis (FIG. 5D) can occur independently of prior botulinum toxin administrations. If the ptosis is due to a prior botulinum toxin administration, it will resolve over 12 weeks. Senile ptosis, with lid drooping and soft tissue excess around the eyelid, is pre-existing and does not change over time.

In some embodiments, the present method prevents non-senile ptosis from recurring or senile ptosis from worsening, the method comprises locating the administration targets, including the corrugators, the procerus, the frontalis, or combinations thereof as disclosed herein, isolating the administration targets so that the botulinum toxin is administered only to the intended target area without inadvertently impacting an adjacent area as disclosed herein; controlling the injection depth, and angling the needle as to aim away from sensitive structures, including the periosteum, as disclosed herein.

In some embodiments, the assessing step comprises inspecting the eyelid and/or the eyebrow of the patient. In some embodiments, the inspecting step comprises determining whether the eyelid is drooping, whether there is excessive skin under the brow and whether the eyebrow depresses or elevates. In some embodiments, the present method further comprises informing the patient of the existence of the ptosis. In some embodiments, the present method further comprises providing a time interval between the assessment step and the administration of the botulinum toxin to the administration target muscles. In some embodiments, the time interval ranges from 1 week to 5 months. In one embodiment, the time interval between the assessment step and the administration step is about 12 weeks. In some embodiments, the time interval is less than 12 weeks. In some embodiments, the time interval is more than 12 weeks. Preferably, as delaying re-treatment may compromise treatment efficacy, in some embodiments, the present method comprises evaluating the patient for ptosis, informing the patient of the pre-existing ptosis condition, and administering a botulinum toxin to the target muscles, wherein the administering is specifically targeted so as to prevent non-senile ptosis from recurring or senile ptosis from worsening, as disclosed herein.

In some embodiments, subsequent to the assessing step for pre-existing ptosis and informing the patient, the present method further comprises administering a botulinum toxin to the target muscles, including and in particular the corrugators, procerus and frontalis muscles, or combinations thereof, wherein the target muscles are carefully isolated as disclosed herein so that the botulinum toxin is administered only to the intended target area without inadvertently impacting an adjacent area; and wherein the injection depth is controlled as disclosed herein, and wherein the needle is specifically angled to aim away from sensitive structures, including the periosteum, as disclosed herein.

Figure 6B:
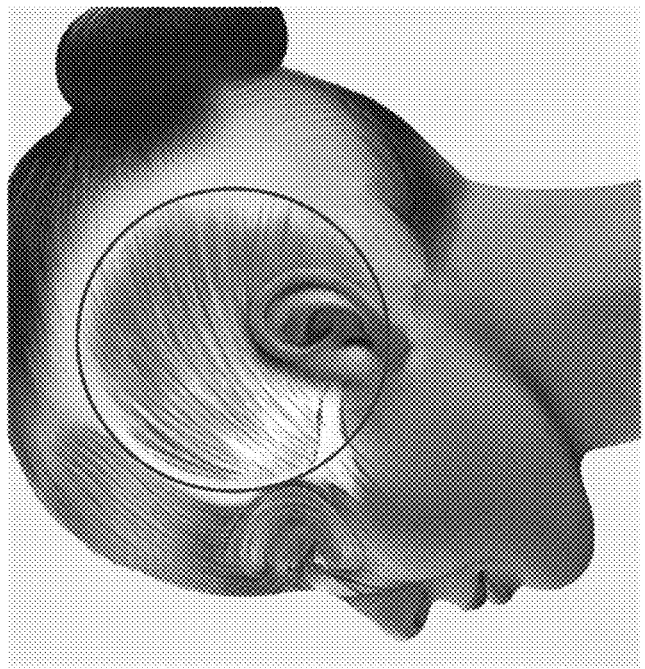
Figure 6A:
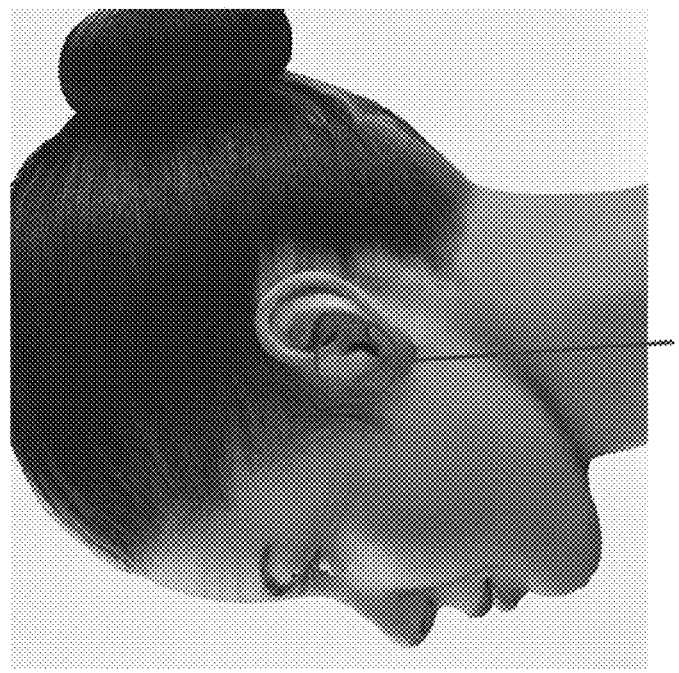
Figure 6D:
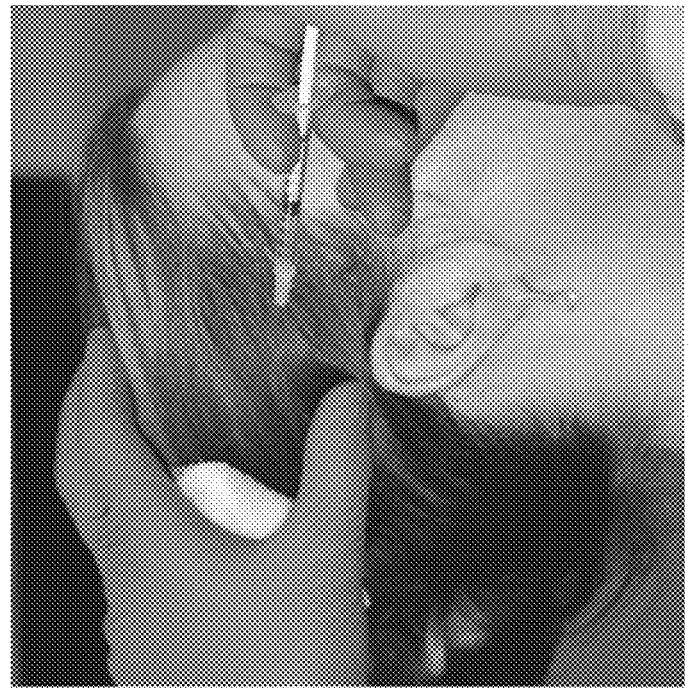
Figure 6C:
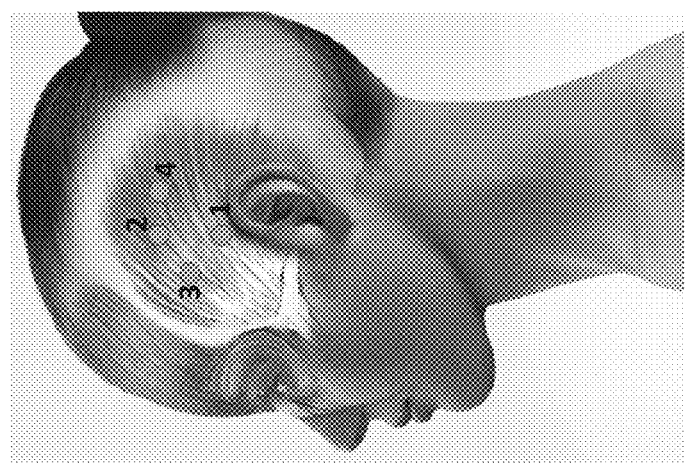

Temporalis:

In one exemplary embodiment, the present method further comprises local administration of a botulinum neurotoxin to the temporalis at about forty units divided among eight sites of injection bilaterally, or 4 sites on each side (as shown in FIG. 6C) up to fifty units divided among ten sites of injection. The tragus is an important landmark for temporalis injections. This muscle area commonly bleeds during injections because it is surrounded by many blood vessels.

In some embodiments, the present method comprises localizing the temporalis and administering a botulinum toxin to the temporalis. In some embodiments, the localizing step comprises locating the tragus. In some embodiments, the localizing step comprises providing instructions to a patient to clench his/her teeth, which activates the temporalis. In some embodiment, the present method comprises localizing a first administration site of the temporalis muscle, the localizing step comprises locating the tragus and moving a finger vertically up the side of the head of the patient about 3 cm (or about 2 fingerbreadths) and injecting the botulinum toxin at the first administration site (FIG. 6C). In some embodiments, the present method further comprises localizing a second administration site of the temporalis muscle, the localizing the second administration site comprises moving vertically in line with the tragus from about 1.5 cm up to about 3 cm (or about 1-2 fingerbreadths) from the first administration site, and injecting the botulinum toxin at the second administration site. In some embodiments, the present method further comprises localizing a third administration site of the temporalis muscle, the localizing the third administration site comprises moving from about 1.5 cm up to about 3 cm (or about 1-2 fingerbreadths) forward toward the face from the first and second administration sites and injecting the botulinum toxin at the third administration site. In some embodiments, the present method further comprises localizing a fourth administration site of the temporalis muscle, the localizing the fourth administration site comprises moving back about 1.5 cm from the second administration site and in line with the midportion (helix) of the ear; and injecting the botulinum toxin at the fourth administration site. In one embodiment, the localizing step further comprises placing a finger in the middle of the helix of the ear to locate the fourth administration site. In some embodiments, the administrating step is carried out as posterior as possible and stays within the hairline, as shown in FIG. 6D. In one embodiment, the local administration of botulinum toxin to the temporalis comprises injecting superficially at a 45° angle, as shown in FIG. 6D. In some embodiments, the present method further comprises applying pressure on the administration site to stop bleeding if bleeding occurs. In some embodiments, the present method further comprises inspecting the patient following administration of the botulinum toxin for bleeding. In some embodiments, the administrating step further comprises drawing back on the needle to assess for a blood flush in the muscle area. In some embodiments, the penetration depth of the needle is controlled such that it remains above the periosteum. In some embodiments, a local and topical anesthetic is administered before administration of the neurotoxin to minimize discomfort.

Figure 7A:
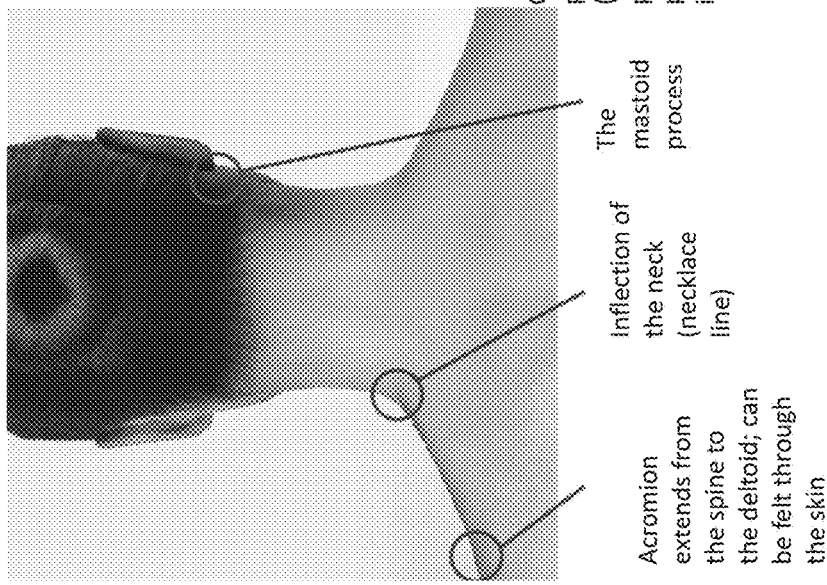
FIGS. 7A and 7B show the back-of-head and neck anatomy, identifying one or more administration target sites thereof in accordance with aspects of the present injection paradigm.
Figure 7B:
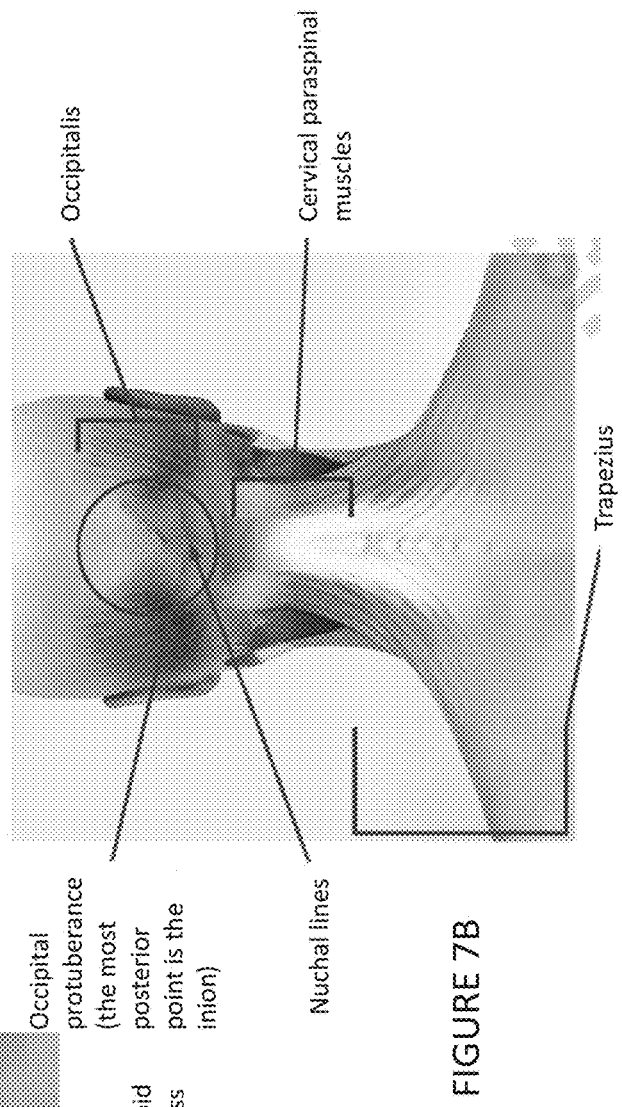

FIGS. 7A and 7B show the back-of-head and neck anatomy, identifying the location of exemplary administration target sites, including the occipitalis, cervical paraspinal and trapezius muscles. As shown in FIG. 7A, several landmarks can be used to localize the administration target sites. For example, the acromion extends from the spine to the deltoid and can be felt through the skin.

Figure 8B:
FIGS. 8A-8B show the administration sites and injection technique for administrating a botulinum toxin into the occipitalis muscle in accordance aspects of the present method.
Figure 8A:
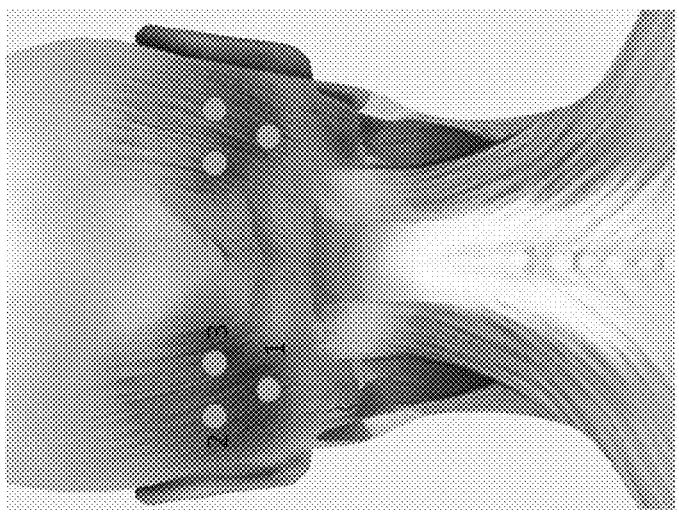

Occipitalis:

In one exemplary embodiment, the present method further comprises local administration of a botulinum neurotoxin to the occipitalis at about thirty units divided among six sites of injection bilaterally, or 3 sites on each side (as shown in FIG. 8A) to about forty units divided among eight sites of injection. The function of the occipitalis is to serve as an anchor for the frontalis. The occipitalis muscles are in proximity of the occipital nerves, which may cause pain in some patients. The occipitalis muscle is shallow. If occipitalis injections are given too low, they can cause neck pain and weakness. The nuchal ridge (FIG. 7B) is an important landmark for occipitalis injections.

In some embodiments, the present method comprises localizing the occipitalis, and administering a botulinum toxin to the occipitalis. In some embodiment, the localizing step comprises locating the nuchal ridge. The present method comprises localizing a first administration site of the occipitalis muscle, the localizing step comprises palpating the occipital protuberance and finding the most posterior point, which is the inion (FIG. 7B); palpating the nuchal ridge and locating the tip of the mastoid process behind the ear (FIG. 7A), placing the thumb on the midpoint of the occipital protuberance (inion) and the index finger on the tip of the mastoid process; dividing the space between the thumb and the index finger in half and identifying a midpoint; and locating the first administration site above the nuchal ridge at the midpoint; and injecting the botulinum toxin at the first administration site. In some embodiments, the present method further comprises localizing a second administration site of the occipitalis muscle, the localizing the second administration site comprises measuring a diagonal fingerbreadth up and out toward the helix of the ear (at the 10 o'clock position), and injecting the botulinum toxin at the second administration site. In some embodiments, the present method further comprises localizing a third administration site of the occipitalis muscle, the localizing the third administration site comprises measuring a diagonal fingerbreadth up and medial (at the 2 o'clock position), and injecting the botulinum toxin at the third administration site. To prevent low occipitalis injections which can cause neck pain and weakness, in a preferred embodiment, the administrating step is carried out above the nuchal ridge. In one embodiment, the local administration of botulinum toxin to the occipitalis comprises injecting superficially at a 45° angle, as shown in FIG. 8B. In some embodiments, the needle is angled upward, away from the neck, as shown in FIG. 8B. In some embodiments, the penetration depth of the needle is controlled such that it is just upon penetration of the dermis. As the occipitalis muscles are in proximity of the occipital nerves, which may cause pain, in some embodiments, a local and topical anesthetic is administered before administration of the neurotoxin to minimize discomfort.

Cervical Paraspinal Muscle Group

Figure 9B:
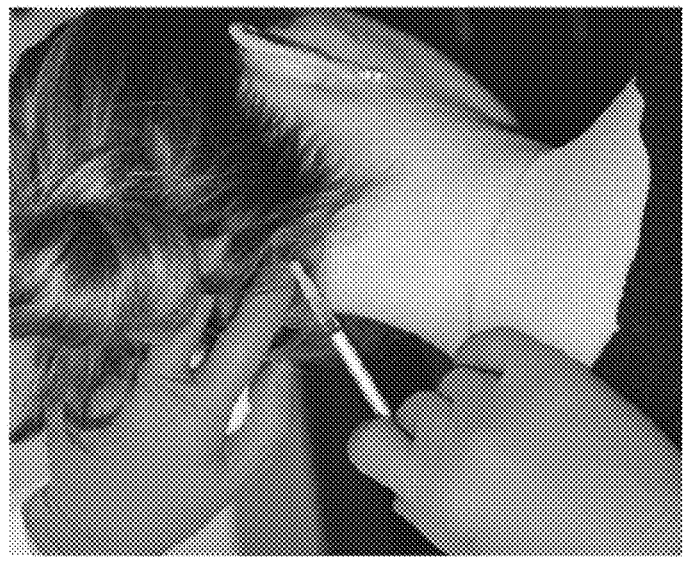
FIGS. 9A-9B show the administration sites and injection technique for administrating a botulinum toxin into the cervical paraspinal muscle group in accordance aspects of the present method.
Figure 9A:
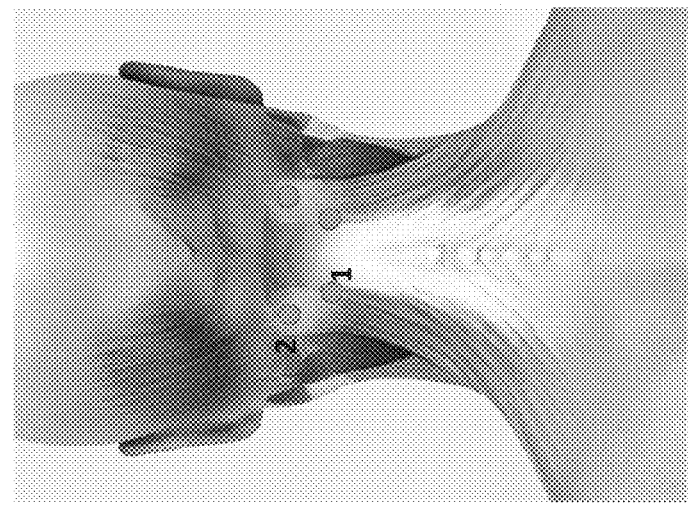

In one exemplary embodiment, the present method further comprises local administration of a botulinum neurotoxin to the cervical paraspinal muscles at about twenty units divided among four sites of injection (as shown in FIG. 9A). The cervical paraspinals should be considered as a muscle group, not a specific muscle. Injecting the cervical paraspinals too low or too deep can lead to muscle weakness. To ensure the muscles are not injected too low, the cervical paraspinals should be considered as suboccipital muscles. In some prior art protocol, the muscle areas for injection are identified by localizing a first administration site of the cervical paraspinals, the localizing step comprises measuring about 1 cm left of the midline of the cervical spine (FIG. 9A) and about 3 cm (or about 2 fingerbreadths) inferior to the occipital protuberance (FIG. 7B); and injecting the botulinum toxin at the first administration site. A second administration site is identified by measuring about 1.5 cm (or about 1 fingerbreadth) diagonally up at a 45° angle toward the helix of the ear from the first injection; and injecting the botulinum toxin at the second administration site. Administrating of the botulinum neurotoxin based solely on the approximated distance or fingerbreadth approach may lead to too low or too deep injections, which can cause muscle weakness.

To minimize or prevent unwarranted side effects, in some embodiments, the present method comprises localizing the cervical paraspinal muscles and administering a botulinum toxin to the cervical paraspinal muscles. In some embodiments, the localizing step comprises visualizing a line across the neck, about 2 fingerbreadths down from the occipital protuberance and injecting above that line. In some embodiments, the localizing step comprises providing instructions to the patient to sit upright, with his/her head in a neutral position. If the neck is flexed far forward, the injections may be too deep. In some embodiments, the administrating step comprises injecting superficially at a 45° angle, as shown in FIG. 9B. In some embodiments, the administrating occurs in the hairline. In some embodiments, the penetration depth of the needle is controlled such that it penetrates the dermis and targets the superficial muscle layer.

In some embodiments, the present method further comprises evaluating the patient for neck weakness and neck pain subsequent to the administrating step, the evaluating comprises positioning the patient upright, with the head in the neutral position, determining whether the neck is flexed far forward. If the neck is flexed far forward, the injections may be too deep. In some embodiments, a local and topical anesthetic is administered before administration of the neurotoxin to minimize discomfort.

Figure 10B:
FIGS. 10A-10B show the administration sites and injection technique for administrating a botulinum toxin into the trapezius muscle in accordance aspects of the present method.
Figure 10A:
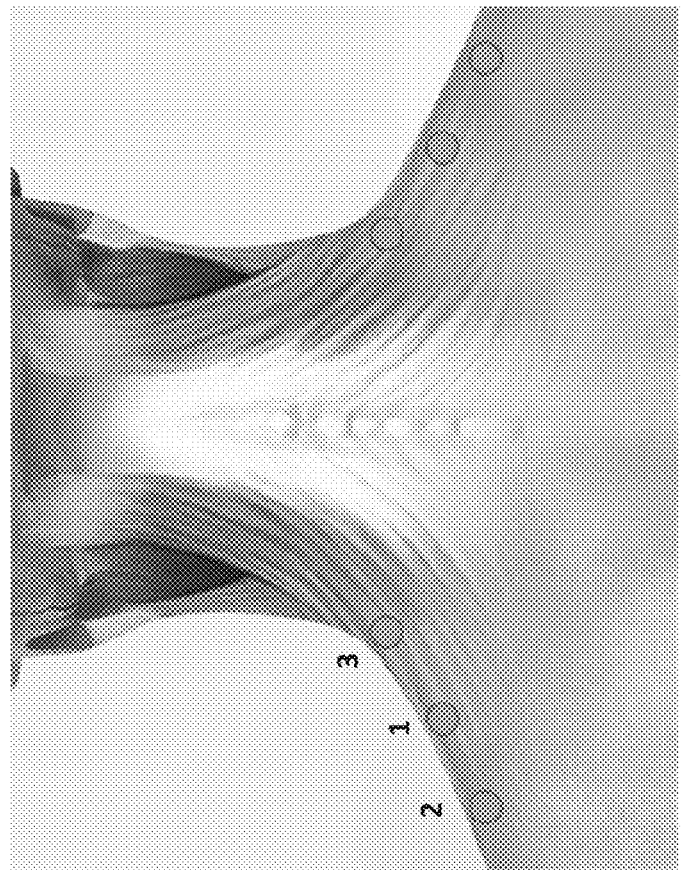

Trapezius:

In one exemplary embodiment, the present method further comprises local administration of a botulinum neurotoxin to the trapezius about thirty units divided among six sites of injection up (as shown in FIG. 10A) to about fifty units divided among ten sites of injection. In some embodiments, the present method comprises localizing a first administration site of the trapezius, the localizing step comprises dividing the upper portion of the trapezius muscle in half, from the inflection point of the neck (necklace line) to the acromion (FIG. 7A), the first administration site is located at this midpoint; and injecting the botulinum toxin at the first administration site. In some embodiments, the present method further comprises localizing a second administration site of the trapezius, the localizing the second administration site comprises splitting the difference between the first injection site and the acromion; and injecting the botulinum toxin at the second administration site. In some embodiments, the present method further comprises localizing a third administration site of the trapezius, the localizing the third administration site comprises splitting the difference between the first injection site and the necklace line.

To prevent or minimize unwarranted side effects, in some embodiments, the local administration of botulinum toxin to the trapezius comprises injecting horizontally to the muscle to avoid injecting too deep, as shown in FIG. 10B. In some embodiments, the local administration of botulinum toxin comprises injecting the supraclavicular portion of the muscle, lateral to the necklace line and medial to the deltoid/acromion joint (FIG. 7A). In some embodiments, a local and topical anesthetic is administered before administration of the neurotoxin to minimize discomfort.

Figure 11:
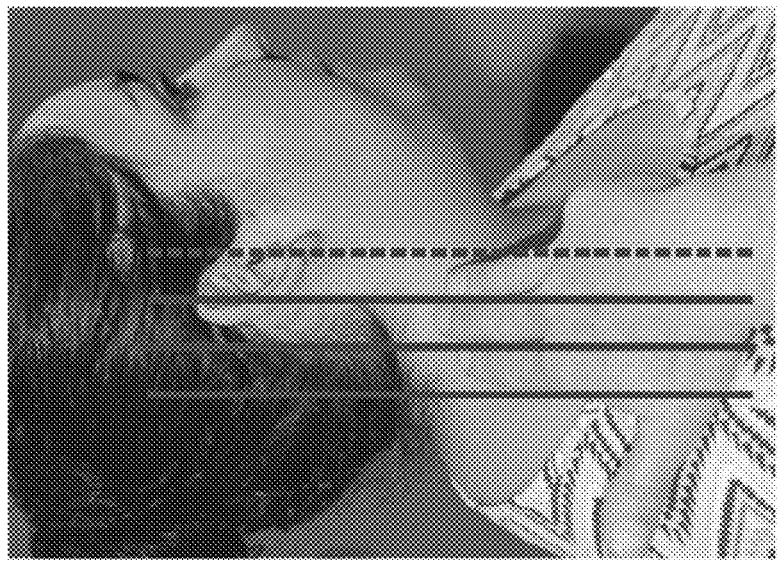
FIG. 11 is a diagram for assessing a patient's neck pain/weakness in accordance with aspects of the present method.

In some embodiments, the present method further comprises evaluating the patient for neck weakness prior to administrating botulinum toxin to the target muscles. In some embodiments, the evaluating step comprises positioning the patient upright, with the head in the neutral position and determining whether the neck is flexed far forward. If the tragus of the ear lines up with the anterior ridge of the trapezius muscle in profile, as shown in FIG. 11, there is no apparent neck weakness. If the tragus of the ear is more than 2 fingerbreadths (~3 cm) from the anterior ridge of the trapezius muscle, that shows neck weakness. In some embodiments, the present method further comprises informing the patient of the neck weakness. In some embodiments, the present method further comprises providing a time interval between the assessment step and the administration of the botulinum toxin to the administration target muscles. In some embodiments, the time interval ranges from 1 week to 5 months. In one embodiment, the time interval between the assessment step and the administration step is about 12 weeks. In some embodiments, the time interval is less than 12 weeks. In some embodiments, the time interval is more than 12 weeks. Preferably, as delaying re-treatment may compromise treatment efficacy, in some embodiments, the present method comprises evaluating the patient for neck weakness, informing the patient of the pre-existing neck weakness condition, and administering a botulinum toxin to the target muscles, wherein the administering is specifically targeted as to prevent or minimize causing additional neck pain or weakness, as disclosed herein.

In some embodiments, subsequent to the evaluating step for neck weakness and the informing step, the present method further comprises administering a botulinum toxin to the target muscles as disclosed herein, wherein the administering to the cervical paraspinal muscle group is targeted within two fingerbreadths (~3 cm) below the occipital protuberance (FIG. 7B) and the administering to the trapezius is targeted to the supraclavicular section (corresponding to the injection sites shown in FIG. 10A) lateral to necklace line (FIG. 7A) to prevent or minimize causing additional neck pain or weakness.

The present method can be used to minimize or prevent adverse effects associated with the administration of a botulinum toxin for treating, alleviating symptoms, or reducing the occurrence of neuropsychiatric disorders (ND), including depression, or medication overuse (MOU) disorders.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is may be measured with an improved quality of life (QOL) or Health-Related Quality of Life (HRQL). QOL can be assessed, for example, using the SF-12 or SF-36 health survey scoring procedures, or the Migraine Specific Quality of Life Questionnarie (MSQ). SF-36 assesses a patient's physical and mental health in the eight domains of physical functioning, role limitations due to physical problems, social functioning, bodily pain, general mental health, role limitations due to emotional problems, vitality and general health perceptions. Scores obtained can be compared to published values available for various general and patient populations. The Migraine-Specific Quality of Life Questionnaire Version 2.1 is one of the most frequently utilized disease-specific tools assessing the impact of migraine on HRQL. The MSQ measures the impact of migraine on the patient's HRQL over the past 4 weeks across three dimensions: Role Function-Restrictive (RR), Role Function-Preventive (RP), and Emotional Function (EF). The MSQ was developed from an expert-based item review of the migraine literature and validated in a clinical sample of 458 new and stable EM patients. In the validation study the MSQ revealed high internal consistency (Cronbach's $\alpha$=0.79 to 0.85), a moderate to strong convergent validity, as well as an adequate discriminant validity. Martin and Colleagues 21 performed a multi-center study that further supported the evidence of a high internal consistency (Cronbach's $\alpha$=0.86 to 0.96), strong reliability and good validity of the 14-item MSQ among 267 participants.

The following non-limiting examples provide those of ordinary skill in the art with specific preferred methods to treat chronic migraine within the scope of the present disclosure, and it is not intended to limit the scope of the invention. In the following examples various modes of non-systemic administration of a Clostridial neurotoxin can be carried out. For example, by intramuscular injection, subcutaneous injection or by implantation of a controlled release implant.

EXAMPLES

The following non-limiting examples provide those of ordinary skill in the art with specific preferred methods to treat conditions within the scope of embodiments of the present invention and are not intended to limit the scope of the invention.

Example 1

In a clinical study for treatment of chronic migraine by onabotulinumtoxinA using an injection protocol disclosed by the '195 patent, it was found that 9% of the patients experienced neck pain and 3-4% of the patient experienced ptosis. In a subsequent study at a local headache center with 100 chronic migraine patients, the following protocol was adopted:

The frontalis injections were done in the upper third of the forehead with needle angle superiorly at 45 degrees. The needle was inserted below the dermis into the superficial muscle layers and not too deep to avoid the periosteum.

The corrugator muscle was injected by having the patient furrow the brow. The muscle was palpated between the thumb and index finger. The medial edge of the corrugator muscle was injected. While pinching the muscle to isolate it, the needle was inserted into the muscle at a 90-degree angle to the plane of the face. This limited any diffusion from the muscle into surrounding areas. The depth of the needle was deep to the dermis, in the superficial muscle, above the periosteum.

Injections into the temporalis muscle can produce temporal wasting. When this occurs in the anterior temporal fossa it produces an hourglass appearance. This was prevented by injecting the temporalis within the hairline, using a vertical line drawn through the tragus of the ear as a landmark for the injections.

If the occipitalis muscle is injected too low it can produce neck weakness and neck pain. To avoid this the muscle was localized as follows: (a) by placing a finger on the tip of the mastoid process (behind the ear) and a thumb on the inion (most prominent posterior protrusion of the skull); (b) splitting the difference between the thumb and index finger in half and locating the midpoint on the nuchal ridge. The occipitalis muscle was injected by angling the needle superiorly at 45 degrees starting at this point. The injections were below the dermis and above the periosteum.

The cervical paraspinal muscles were injected superficially and high in the sub-occipital region to avoid neck weakness and neck pain. The injection sites were 2 horizontal fingerbreadths (3 cm) below the occipital protuberance in the midline. The needle was angled superiorly at 45 degrees, inserted just below the dermis.

The trapezius muscles were injected in the supraclavicular region to avoid neck weakness and neck pain. The trapezius muscle has an inflection point at the necklace line. This was used as a landmark together with the acromion. An index finger was placed in the groove of the acromion joint and the necklace line. The distance between the acromion and necklace line are split in half for placement of the first injection was split in half. At this point the first injection was done, at a 0 to 45° angle to avoid a deep injection. The injection was just below the dermis in the superficial muscle layers. The second and third injections were done medial and lateral to the first in an equidistant fashion.

The adverse event rates for the 100 patients receiving the above-described protocol were 1% for the brow ptosis and 4% for the neck pain.

Example 2

A 50 year old woman with CM has been injected with onabotulinumtoxinA by another neurologist on one occasion. She reported that her brow was depressed and her neck was weak with associated pain. This developed 2 weeks after her treatment and persisted for 6 weeks before gradually resolving. She wanted to continue onabotulinumtoxinA treatment for CM but did not want her neck/shoulder or forehead regions to be re-injected.

After educating the patient about the injection protocol described in Example 1 with careful attention to the portion of the muscles that need to be injected to maximize efficacy and decrease side effects, she agreed to proceed. The protocol described in Example 1 was used to treat her. She returned at 6 weeks and reported no brow ptosis or neck pain. Her headaches were reducing and she was satisfied to continue forward to her third onabotulinumtoxinA treatment in 6 week time.

Many alterations and modifications may be made by those having ordinary skill in the art, without departing from the spirit and scope of the disclosure. Therefore, it must be understood that the described embodiments have been set forth only for the purposes of examples, and that the embodiments should not be taken as limiting the scope of the following claims. The following claims are, therefore, to be read to include not only the combination of elements which are literally set forth, but all equivalent elements for performing substantially the same function in substantially the same way to obtain substantially the same result. The claims are thus to be understood to include those that have been described above, those that are conceptually equivalent, and those that incorporate the ideas of the disclosure.

We claim:

1. A method for alleviating or reducing the occurrence of a headache in a patient with chronic migraine headaches, the method comprises:
    localizing one or more administration targets;
    isolating the one or more administration targets; wherein the isolating step isolates the one or more administration targets from an adjacent area;
    administering a therapeutically effective amount of a clostridial toxin to the one or more isolated administration targets;
    wherein the one or more administration targets comprise the frontalis, corrugator, procerus, occipitalis, temporalis, trapezius and cervical paraspinal muscles;
    wherein the administrating step is by injection and wherein the administering step comprises injecting superficially at a 90° angle into the corrugator muscles; thereby alleviating or reducing the occurrence of the headache in the patient.

2. The method of claim 1, wherein the isolating the corrugator muscle comprises providing instructions to the patient to furrow her/his brow, palpating and pinching the corrugator muscle, holding the corrugator muscle between the thumb and index finger.

3. The method of claim 1, wherein the isolating the procerus muscle comprises providing instructions to the patient to furrow her/his brow, using the resulting vertical and horizontal lines as orientation lines.

4. The method of claim 1, wherein the administering to the procerus muscle comprises targeting the belly of the procerus muscle, injecting superficially at a 90° angle into the procerus, and controlling the penetration depth of the needle such that it remains above the periosteum.

5. The method of claim 1, wherein the isolating the frontalis muscle comprises providing instructions to the patient to raising her/his eyebrows and skin over the root of the nose in an attempt to create an expression of surprise and identifying the upper third of the forehead.

6. The method of claim 1, wherein the administrating step to the frontalis comprises angling the needle superiorly at a 45° angle into the frontalis muscle and injecting superficially by controlling the penetration depth of the needle such that it remains above the periosteum.

7. The method of claim 1, wherein the localizing the cervical paraspinal muscles comprises providing instructions to the patient to sit upright, with his/her head in a neutral position, visualizing a line across the patient's neck about 2 fingerbreadths down from the occipital protuberance.

8. The method of claim 7, wherein the administrating step to the cervical paraspinal comprises injecting superficially at a 45° angle above the visualized line about 2 fingerbreadths down from the patient's occipital protuberance.

9. The method of claim 1, wherein the administrating to the trapezius muscle comprises injecting horizontally to the trapezius muscle.

10. The method of claim 1, wherein the administrating to the trapezius muscle comprises injecting the supraclavicular portion of the muscle, lateral to the necklace line and medial to the deltoid/acromion joint.

11. The method of claim 1, wherein the clostridial toxin is a botulinum toxin.

12. A method for minimizing adverse effects associated with the administration of a clostridial toxin for treating or alleviating a headache in a patient with chronic migraine, the method comprises locating one or more administration targets, isolating the one or more administration targets, administering a therapeutically effective amount of a clostridial toxin to the one or more isolated administration targets; wherein the one or more administration targets comprise the frontalis, corrugator, procerus, occipitalis, temporalis, trapezius and cervical paraspinal muscles;
wherein the isolating step isolates the one or more administration targets from an adjacent area; and
wherein the administrating step comprises injecting superficially at a 90° angle into the corrugator muscles; thereby minimizing adverse effects associated with the administration of the clostridial toxin.

13. The method of claim 12, wherein the adverse effects comprise ptosis, neck pain and/or weakness, headache, or combinations thereof.

14. The method of claim 12, wherein the clostridial toxin is a botulinum toxin.

15. A method for improving efficacy of headache treatment by a clostridial toxin in a patient in need thereof by minimizing one or more adverse effects associated with clostridial toxin administration, comprising localizing one or more administration targets, isolating the one or more administration targets, administering a therapeutically effective amount of the clostridial toxin to the isolated one or more administration targets; wherein the isolating step isolates the one or more administration targets from an adjacent area; wherein the one or more administration targets comprise the frontalis, corrugator, procerus, occipitalis, temporalis, trapezius and cervical paraspinal muscles; and wherein the administrating comprises injecting superficially at a 90° angle into the belly of the corrugator muscles; thereby preventing or minimizing unwarranted adverse effects and improving efficacy of headache treatment.

16. The method of claim 15, wherein the adverse effects comprise ptosis, neck pain, neck weakness, headaches, or combinations thereof.

17. The method of claim 15, further comprising evaluating the patient of manifestation of the one or more adverse effects prior to the localizing, isolating and administrating steps.

18. The method of claim 15, wherein the clostridial toxin is a botulinum toxin.

19. A method for treating or reducing the occurrence of a headache in a patient with chronic migraine headaches, the method comprising:
local administration of a botulinum neurotoxin to 31 fixed injection sites across seven head and neck muscles, and optionally up to 8 additional injection sites into three specific muscles, wherein these three muscles are subset of the seven head and neck muscles,
wherein the 31 fixed injection sites comprise the frontalis, corrugator, procerus, occipitalis, temporalis, trapezius and cervical paraspinal muscles; and
wherein the administration is by injection and comprises injecting superficially at a 90° angle into the corrugator muscles; thereby alleviating or reducing the occurrence of the headache in the patient; to thereby treat or reduce the occurrence of chronic migraine headache in the patient.

20. The method of claim 19, wherein the botulinum neurotoxin is serotype A.

21. The method of claim 20, wherein the botulinum neurotoxin type A is onabotulinumtoxinA.

22. The method of claim 21, wherein the total amount of botulinum toxin type A administered is from about 155 units to about 195 units of onabotulinumtoxinA.

23. The method of claim 20, wherein the botulinum neurotoxin type A is abobotulinumtoxinA.

24. The method of claim 19, wherein the botulinum neurotoxin is a pure botulinum toxin.

25. The method of claim 24, wherein the pure botulinum neurotoxin is incobotulinumtoxinA.

26. The method of claim 19, wherein the botulinum neurotoxin is serotype B.

27. The method of claim 19, wherein the botulinum neurotoxin is type E.

28. The method of claim 19, wherein the administration is by subcutaneous injection.

29. The method of claim 19, wherein the administration is by intramuscular injection.

* * * * *